(12) United States Patent
Joedicke

(10) Patent No.: US 7,060,658 B2
(45) Date of Patent: Jun. 13, 2006

(54) ROOFING GRANULES

(75) Inventor: Ingo B. Joedicke, Falling Waters, WV (US)

(73) Assignee: ISP Investments Inc., Wilmington, DE (US)

( * ) Notice: Subject to any disclaimer, the term of this patent is extended or adjusted under 35 U.S.C. 154(b) by 332 days.

(21) Appl. No.: 10/717,836

(22) Filed: Nov. 20, 2003

(65) Prior Publication Data

US 2004/0110639 A1    Jun. 10, 2004

Related U.S. Application Data

(60) Provisional application No. 60/429,464, filed on Nov. 27, 2002.

(51) Int. Cl.
| | |
|---|---|
| *A01N 59/16* | (2006.01) |
| *A01N 25/12* | (2006.01) |
| *B32B 5/16* | (2006.01) |
| *B32B 5/22* | (2006.01) |
| *B32B 9/04* | (2006.01) |
| *B32B 9/00* | (2006.01) |
| *B05D 1/38* | (2006.01) |

(52) U.S. Cl. ............... 504/151; 504/152; 504/367; 424/490; 424/635; 424/641; 428/403; 428/142; 428/144; 428/145; 428/148; 428/149; 427/186; 427/205; 106/15.05; 106/18.36

(58) Field of Classification Search ............... 504/151, 504/152, 367; 424/490, 635, 641; 428/403, 428/142, 144, 145, 148, 149; 427/186, 205; 106/15.05, 18.36

See application file for complete search history.

(56) References Cited

U.S. PATENT DOCUMENTS

| | | | |
|---|---|---|---|
| 2,732,311 A | 1/1956 | Hartwright | 427/186 |
| 3,894,877 A | 7/1975 | Nelson | 106/18 |
| 4,092,441 A | 5/1978 | Meyer et al. | 427/453 |
| 4,378,403 A | 3/1983 | Kotcharian | 442/234 |
| 4,378,408 A * | 3/1983 | Joedicke | 428/403 |
| 5,356,664 A | 10/1994 | Narayan et al. | 427/186 |
| 5,411,803 A | 5/1995 | George et al. | 428/403 |
| 6,214,466 B1 | 4/2001 | Joedicke | 428/404 |
| 6,235,372 B1 * | 5/2001 | Joedicke | 428/145 |
| 2002/0098983 A1 * | 7/2002 | Pursell et al. | 504/367 |

* cited by examiner

*Primary Examiner*—John Pak
(74) *Attorney, Agent, or Firm*—William J. Davis; Imre Balogh

(57) ABSTRACT

Use of internal gas-forming compound to adjust coating porosity to control copper release rates in algae-retardant roofing granule products.

9 Claims, 1 Drawing Sheet

Effect of Outer Coating Porosity Enhancement

ROOFING GRANULES

CROSS-REFERENCE TO RELATED APPLICATIONS

This application is a continuation-in-part of provisional Application Ser. No. 60/429,464 filed on Nov. 27, 2002, now abandoned.

BACKGROUND OF THE INVENTION

1. Field of the Invention

This invention relates to algae-retardant roofing granules having algicidal properties. More particularly, the invention relates to a two-coat product having: an inner coat containing a slow-release copper or bimetallic copper/zinc algaecides; and an outer coat having copper or bimetallic copper/zinc algaecides containing gas-forming compounds which form a network of micro voids to increase porosity and thereby facilitate leaching of the algaecides to enhance their algicidal properties.

2. Reported Development

Roofing granules, both natural and artificially colored granules, are extensively used in roll roofing and asphalt shingle compositions. The roofing granules are embedded in the asphalt coating on the surface of the asphalt-impregnated felt base material, the granules thus forming a coating that provides an adherent, weather-resistant exterior roofing surface.

Mineral-surfaced asphalt shingle roofing can support the growth of discoloring algae, most commonly of the blue-green type (Cyanobacteria). Such roofs can develop spots of algae colonies within 2–3 years of exposure, particularly in the southeastern gulf states, as a result of inoculation by air-born desiccated cells. These spots gradually grow into unsightly streaks as rain washes cells down the roof. In severe cases, this discoloration will eventually overtake the entire roof.

In addition to being unsightly, algae discoloration reduces the reflectivity of light-colored asphalt shingles and thus increases their peak daytime temperatures. Some have argued that his can reduce the effective service life of the roof. Although algae discoloration can be removed by cleaning, this process is costly and will have to be repeated every few years. A more effective approach is to utilize algae-retardant roofing granules as a component of the asphalt shingles to prevent the growth of discoloring algae in the first place.

Illustrative examples of prior art compositions used in concert with roof shingles are as follows.

U.S. Pat. No. 2,732,311 discloses the use of metallic flakes, such as aluminum, copper and bronze flakes to produce radiation-reflective roofing granules.

U.S. Pat. No. 3,894,877 discloses incorporating copper silicate into color coated roofing granules using heavy processing oil to have the copper silicate adsorbed into the color coat.

U.S. Pat. No. 4,092,441 discloses roofing granule treatment by coating the roofing granules with metallic algaecides such as zinc, copper, nickel and mixtures thereof which are sprayed in the form of molten droplets onto the surface of the roofing granules or onto the surface of asphalt roofing.

U.S. Pat. No. 4,378,403 discloses roofing granules coated with insolubilized reaction product of a coating compositions comprising water, kaolin clay, sodium silicate, pigment, and gas-forming compounds. The gas forming compound includes hydrogen peroxide, alkali metal perborates, alkali metal persulfates, alkali metal borohydrides, and alkali metal azides, and are used for the purpose of enhancing the opacity of the coating.

U.S. Pat. No. 5,356,664 discloses a method of inhibiting algae growth on an asphalt shingle surface using a blend of copper-containing algae-resistant and non-algae-resistance granules.

U.S. Pat. No. 5,411,803 discloses three-layer coated ceramic granules. The ceramic granules comprise the reaction product of an alkali metal silicate and aluminum silicate. The ceramic coating further includes a borate compound and zinc oxide.

U.S. Pat. No. 6,214,466 discloses algae-resistant roofing granules coated with: a first coat consisting of a fired silicate-clay matrix containing cuprous oxide and zinc sulfide to provide a slow, long-term bimetallic copper and zinc ions release; and a second coat consisting of a fired silicate-clay matrix containing a pigment.

Algae-retardant granules currently available include those in which a substantial loading of cuprous oxide (by itself or in combination with zinc compound) is incorporated in some of the semi-ceramic coatings that encapsulate a crushed rock base. At least two (2), and sometimes three (3), ceramic coatings are used in which the cuprous/zinc compounds are incorporated in the inner coating(s) and inorganic pigments, which determine the overall product color, are incorporated in the outer coating. These products are designed to be blended with standard granules at a 10–15% rate and to provide a continuous release of algicidal copper/zinc inons in the presence of moisture from rain and dew. However, the rate of copper/zinc release is often insufficient despite the high loading of cuprous/zinc compounds, due to low porosity of the outer coating, which acts as a barrier to copper/zinc ion migration. This can result in premature failure of the algae-retardant granules and the appearance of unsightly discoloration.

SUMMARY OF THE INVENTION

Roofing shingles typically comprise materials, such as felt and fiberglass, to which asphalt is applied to permeate the felt or fiberglass. Over the impregnated felt or fiberglass mineral granules are applied completing the conventional roofing shingles. The granules are obtained from natural base rocks such as greenstone, rhyolite, andesite, basalt, nephaline syenite, and the like.

Algae-retardant roofing granules of the present invention are artificially-colored mineral aggregate containing slow-release copper or bimetallic copper/zinc algaecides as components of the first coat of a two-coat product. The second, or outer coating, contains the pigments that determine the overall color of the product. This outer coating represents an advance in the art by having a high degree of porosity to increase the rate of copper/zinc leaching to enhance algicidal performance. This high degree of porosity is achieved by incorporating internal gas-forming compounds in the coating composition to form an extensive network of microvoids during the film firing process. The use of internal gas-forming compounds to create microvoids in roofing granule coatings for the purpose of increasing opacity to provide white pigment cost savings is the subject of U.S. Pat. No. 4,378,408 which is incorporated herein in its entirely by reference.

The gas forming compounds of the present invention for rendering the second or outer coating porous and thereby increasing the rate of algicidal leaching, includes a member selected from the group consisting of hydrogen peroxide, alkali metal perborates, alkali metal persulfates, alkali metal borohydrides, and alkali metal azides. The gas forming compound is present in the second or outer coating in the amount of from 0.25% w/w to about 2.5% w/w based on the dry weight of the coating composition.

The second or outer coating comprises a semi-ceramic composition consisting of the following in units of PPT: 10–50 water, 0.25–2.5 internal gas forming compound, 0.25–2.5 solubilizer/stabilizer, 30–60 sodium silicate, and 20–35 clay.

The pigments include: carbon black, titanium dioxide, chromium oxide, yellow iron oxide, ultramarine blue, red iron oxides, black iron oxide, chrome titanate, and metal ferrite.

The average of the voids in the second or outer coating is from about 0.05 micron to about 0.5 micron thick. It is preferred that the second or outer coating is void of algaecides, however, optionally, the second or outer coating may contain those algaecides described in connection with the first or inner coating.

The roofing granules of the present invention comprise the following components.

1. A base of crushed mineral aggregate suitable for roofing granules manufacture. This can be any of the common natural base rocks such as greenstone, rhyolite, andesite, basalt, nephaline syenite, and the like. Suitable synthetic bases, such as coal slags, can also be employed.
2. The base material is coated with a first (inner) layer of semi-ceramic composition consisting of a fired silicate-clay mixture containing cuprous oxide ($Cu_2O$) as a source for slow-release copper. Optionally, a combination of cuprous oxide ($Cu_2O$) and zinc sulfide (ZnS) can be employed as a source of bimetallic slow-release copper and zinc. The cuprous oxide is present in the amounts of 80 pounds up to as high as 180 pounds, and preferably 100–150 pounds per ton (PPT) of base material. The zinc sulfide, when used in conjunction with cuprous oxide, is present in the amounts of from about 5 pounds and up to as high as 40 pounds, and preferably 12–25 PPT of base material.
3. A second (outer) layer of semi-ceramic composition also consisting of a fired silicate-clay matrix containing coloring pigments that determine the overall appearance of the granules. This structure of this coating consists of an extensive network of microvoids that greatly increase porosity to enhance migration of copper/zinc ions from the inner coating in the presence of moisture.

The essential steps in the manufacturing process of the roofing granules of the present invention are as follows.

1. The crushed and sized base aggregate (typically No. 11 grading) is heated to 210° F.–230° F.
2. The preheated granules are then coated with a "first coat" semi-ceramic composition, of which the following is typical in units of pounds per ton (PPT) or gms per 2000 gm of base aggregate:

| Water | 40 |
|---|---|
| Sodium Silicate Solution | 75 |
| (38% solids, $SiO_2/Na_2O$ = 2.9) | |
| Kaolin Clay | 35 |
| Pigments | 0–10 |
| Cuprous Oxide | 80–150 |
| Zinc Sulfide | 0–25 |

These components are combined into a slurry by using suitable mixing equipment. The slurry is then applied to the preheated base aggregate in a suitable apparatus to produce individually first-coated granules.

3. The first-coated granules are pre-dried by adjusting temperature and air flow to reduce their moisture content to between 0.2%–0.5% w/w.
4. The first coated granules are kiln-fired between 740° F.–760° F. to form an insolubilized silicate-clay matrix coating in which the cuprous oxide, zinc sulfide, and pigments are uniformly distributed.
5. The fired first-coat granules are cooled by means of air flow and/or water application in a suitable apparatus to reduce their temperature to 210° F.–230° F., i.e. back to pre-heat conditions in preparation for application for the outer coating.
6. The preheated granules are next coated with a "outer coat" semi-ceramic compositions of which the following is typical (units in PPT):

| Water | 25 |
|---|---|
| Internal Gas-Forming Compound | 0.5–1.5 |
| Solubilizer/Stabilizer | 0.5–1.5 |
| Sodium Silicate Solution | 56 |
| (40% Solids, $SiO_2/Na_2O$ = 2.5) | |
| Kaolin Clay | 25 |
| Pigments | 0–15 |

As before, these compounds are also combined into a slurry by using suitable mixing equipment. The internal gas-forming compound and solubilizer/stabilizer are most conveniently and effectively dissolved in the water prior to addition of the sodium silicate and other slurry components.

The mixed slurry is then applied to the preheated base aggregate in a suitable apparatus to produce individually outer-coated granules.

7. The outer-coated granules are pre-dried by adjusting temperature and air flow to reduce their moisture content to between 0.2%–0.5% w/w.
8. The outer-coated granules are kiln-fired at between 890° F.–910° F. to form an insolubilized silicate-clay matrix coating in which the pigments are uniformly distributed. This coating will also have a higher level of porosity than that of standard silicate/clay coatings as a result of the inclusion of internal gas-forming compounds, which create an extensive network of microvoids in the coating during the kiln-firing process.
9. The fired outer-coated granules are cooled by means of air flow and/or water application in a suitable apparatus to reduce their temperature to 200° F.–220° F.
10. The color-coated, algae-retardant granules are treated with a mixture of process oil and an organosilicon compound to impart dust control and to improve asphalt adhesion.

Internal Gas-Forming Compound and Solubilizer/Stabilizer

The preferred soluble gas-forming compound is sodium perborate tetrahydrate ($NaBO_3$). When used in concert with boric acid ($H_3BO_3$) it dissolves readily in water and is compatible with excess sodium silicate. It decomposes during the drying process to form microscopic $O_2$ gas bubbles, which create the extensive network of porosity-enhancing microvoids in the coating during the kiln firing process. A mixture of 35–50% hydrogen peroxide ($H_2O_2$) in concert with borax ($NaBO_2.10H_2O$) stabilizer will give similar results by the same process. Also usable as an internal gas source are sodium azide (NaN$_3$) and sodium borohydride (NaBH4), which are of much higher cost.

DESCRIPTION OF THE PREFERRED EMBODIMENTS

Figure 1:
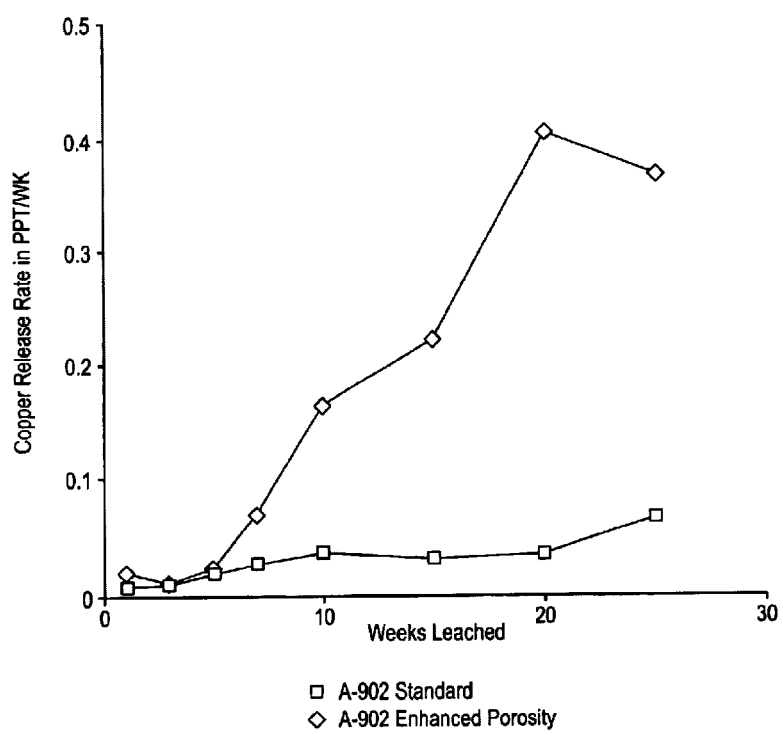
FIG. 1 shows the result of copper leaching studies of a standard coating versus a coating of enhanced porosity.

This invention involves the presence of microvoids in the second coating of the granules to enhance the migration of algaecides contained in the first coating thereby providing increased algicidal activity on the surface of the granules.

EXAMPLES

A. Algae-Resistant A-902 Granules of Enhanced Porosity

In a laboratory pilot plant, the following first-coat composition was applied to 1000 gms of rhyolite base rock that was preheated to 180°–200° F.

| | |
|---|---|
| Water | 20.0 |
| Sodium Silicate | 37.5 |
| (39% solids, SiO$_2$/Na$_2$O = 2.8–3.0) | |
| Titanium Oxide | 5.0 |
| Cuprous Oxide | 45.0 |
| Kaolin Clay | 17.5 |
| Total: | 125.0 gm |

This mixture of granules and coating composition was placed in a sealed jar of 1-quart capacity and placed on a paint shaker for 1 minute of vigorous agitation. The coated granules were transferred to an aluminum tray and heated with a hot air gun while mixing with a large spatula to remove all solvent water from the coated granules. The dried, free-flowing granules were then sent through a small rotary kiln and fired at 704° F.–760° F. These fired first-coat granules were then coated with the following second-coat composition:

| | |
|---|---|
| Water | 13.4 |
| Sodium Perborate | 0.5 |
| Boric Acid | 0.5 |
| Sodium silicate | 28.0 |
| (41% solids, SiO$_2$/Na$_2$O = 2.5) | |
| Titanium Dioxide | 5.0 |
| Chrome Oxide | 0.4 |
| Ultramarine blue | 2.0 |
| Kaolin clay | 12.5 |
| Total: | 62.32 gm |

This mixture of granules and coating composition was similarly mixed and pre-dried to produce free-flowing granules, which were subsequently sent through a small rotary kiln fired at 890°–910° F. These fired second-coat granules were then cooled. To produce finished granules, a standard post-treatment of process oil and polysiloxane was applied. The resulting A-902 light-colored algae-resistant roofing granules are comparable to those produced commercially by large-scale manufacturing equipment and meet all established color and quality specification.

B. Algae-Resistant A-901 Granules of Enhanced Porosity

The dark-colored counterpart to the product made in Example A is A-901, which is made by the same process but with modified pigments and loadings to produce an accent-colored product.

PERFORMANCE EVALUATION DATA

A. Effect of Porosity Enhancement on Copper Leach Rate

The Soxhlet leaching profile for A-902 with enhanced outer coating porosity (made in accordance with Example A above) is shown in FIG. 1 in comparison with A-902 control that was made with a standard outer coating. The A-902 of enhanced outer coating develops a copper release rate that is significantly higher than that of the control.

The details of the laboratory procedure used in the Soxhlet leaching study is shown hereunder in steps 1–4, and the result of the study is shown in the FIG. 1 drawing.

1. A-902 granules without post treatment were screened to pass a Tyler 10 mesh screen and retained on a 20 mesh screen.
2. 100 gm of the A-902 granules were placed in a heavy wall paper thimble and inserted into a Soxhlet extraction apparatus. A heating mantle-jacketed 500 ml flask, initially containing distilled water, was attached to the Soxhlet extractor.
3. Extractions were allowed to proceed at a rate of 2–3 cycles per hour for one week, at which time the leachate solution in the flask was removed and replaced with fresh distilled water. Extraction was then resumed for another week after which the leachate collection was again repeated every week for 25–30 weeks.
4. Leachate solutions were adjusted to pH 2.0 with 2N nitric acid, filtered through #4 Whatman filter paper, and brought to a total volume of 500 ml with distilled water. The final solution was then quantitatively analyzed for copper using atomic absorption. These weekly increments of copper release were plotted as a function of leaching time to produce Soxhlet leaching profiles.

FIG. 1 shows the results of copper leaching studies of a standard coating versus a coating of enhanced porosity of the present invention wherein: the copper release rate in PPT is shown on the ordinate (y-axis), and the weeks leached is shown on the abscissa (x-axis).

B. Liquid Algae Culture Studies

Pilot Plant Products

A-901 and A-902 products were made in the pilot plant in accordance with the descriptions in Examples A & B above. The cuprous oxide content of the coat was first adjusted to produce finished product copper contents of 3.6% and 5.3%. The porosity of the outer coating was enhanced via sodium perborate/boric acid inclusion. Standard A-901 and A-902, without outer coating porosity enhancement, were also produced for use as controls.

To determine the effect of both "standard" and "porosity-enhanced" A-901/A-902 products on actual algae growth rates, the following procedure was used:

1. A-901 and A-902 granules under test were applied as a ⅛" layer onto asphalt-coated aluminum panels measuring 2.5"×6.0". The panels were placed in an approximately 240° F. air circulating ovenfor about 5 minutes to soften the asphalt. The panels were removed from the oven and the granules pressed into the softened asphalt and rolled into a smooth layer by means of a PVC rolling pin.

2. The granule-surfaced panels were placed in an Atlas 3000I weatherometer and exposed to a conventional weathering cycle for 1000 hours to condition the granules by simulating a period of weathering.
3. After removal from the weatherometer, the granules were extracted from the panels by dissolving the asphalt. The granules were briefly washed with boiling water and then dried. The A-901 granules were blended with standard accent tone granules at 10%, 12.5% and 15% blend rates. Similarly, the A-902 granules were blended with standard white granules, also at 10%, 12.5% and 15% blend rates.
4. 25.0 gm of each blend was placed in a 500 ml Erlenmeyer flask containing 200 ml of nutrient solution BG 11. The flasks were autoclaved for 15 minutes. BG11 is an algae medium composition containing the following ingredients (see Stanier, R. Y., Kunisawa, R., Mandel, M. and Cohen-Bazire, G., "Purification and properties of unicellular blue-green algae (order Chroococcales)", Bacteriological Review, 35, 171–205:

| | |
|---|---|
| $NaNO_3$ | 1.50 g |
| $K_2HPO_4$ | 0.04 g |
| $MgSO_6 \cdot 7H_2O$ | 0.075 g |
| $CaCl_2 \cdot 2H_2O$ | 0.036 g |
| Citric Acid | 0.006 g |
| Ferric Ammonium Citrate | 0.006 g |
| $Na_2CO_3$ | 0.02 g |
| A-5 micronutrients | 1.0 ml |
| Distilled Water to 1.0 liter | |
| Adjust pH to 7.1 | |

The A-5 micronutrients are as follows:

| | |
|---|---|
| $H_3BO_3$ | 2.86 g |
| $MnCl_2 \cdot 4H_2O$ | 1.81 g |
| $ZnSO_4 \cdot 7H_2O$ | 0.222 g |
| $Na_2MoO_4 \cdot 2H_2O$ | 0.39 g |
| $CuSO_4 \cdot 5H_2$ | 0.079 g |
| $Co(NO_3)_2 \cdot 6H_2O$ | 0.0494 g |
| Distilled water to 1.0 liter | |

5. The liquid culture solutions containing the granule blend samples were inoculated with an algae stock solution that was developed from a discolored roof in the Tampa, Fla. area. This algae stock contained a mixture of unicellular Gloeocapsa and filamentous Phormidium Cyanobacteria. The flask were then placed on a shaker table in a chamber of constant temperature and illumination.
6. After 5 weeks, quantitative chlorophyll measurements were made spectrophotometrically to ascertain algae growth rates, which are tabulated below:

| PRODUCT | COPPER CONTENT | OUTER COATING POROSITY | BLEND RATE | CHLOROPHYLL Microgram/ml |
|---|---|---|---|---|
| A-901 | 3.6% | Standard | 10% | 12.55 |
| A-901 | 3.6% | Standard | 12.5% | 2.14 |
| A-901 | 3.6% | Standard | 15% | 2.50 |
| A-901 | 3.6% | Enhanced | 10% | 1.58 |
| A-901 | 3.6% | Enhanced | 12.5% | 1.00 |
| A-901 | 3.6% | Enhanced | 15% | 0.73 |
| A-902 | 3.6% | Standard | 12.5% | 6.10 |
| A-902 | 3.6% | Standard | 15% | 4.87 |
| A-902 | 3.6% | Enhanced | 12.5% | 1.73 |
| A-902 | 3.6% | Enhanced | 15% | 0.88 |
| A-901 | 5.3% | Standard | 12.5% | 1.02 |
| A-901 | 5.3% | Standard | 15% | 3.30 |
| A-901 | 5.3% | Enhanced | 12.5% | 0.50 |
| A-901 | 5.3% | Enhanced | 15% | 1.10 |
| A-902 | 5.3% | Standard | 10% | 4.50 |
| A-902 | 5.3% | Standard | 12.5% | 3.97 |
| A-902 | 5.3% | Standard | 15% | 3.60 |
| A-902 | 5.3% | Enhanced | 10% | 3.42 |
| A-902 | 5.3% | Enhanced | 12.5% | 0.96 |
| A-902 | 5.3% | Enhanced | 15% | 1.90 |

These results show that, in all cases, enhancement of outer coating porosity by sodium perborate/boric acid inclusion results in reduced chlorophyll, i.e. less total algae present in the nutrient solutions. This is consistent with the results of leaching studies of part IVA, above, in which higher copper ion release resulted from outer coating porosity enhancement.

Liquid Algae Culture Studies—Commercial A-901

A-901, both with standard and porosity enhanced coatings, was commercially produced at the ISP Roofing Granules Manufacturing Plant in Annapolis, Mo. In both cases, the $1^{st}$ coat formulations consisted of the following components in pounds per 2000 lbs base granules:

| | |
|---|---|
| Water | 40 |
| Sodium Silicate Solution | 75 |
| (38% solids, SiO2/Na2O = 2.9) | |
| Kaolin clay | 35 |
| Cuprous Oxide | 100 |

Base granules were coated with this composition and processed as described in Example A. The granules were then further coated with a $2^{nd}$ coat formulation, consisting of the following components in pounds per 2000 lb base granules, and processed to produce A-901 of "enhanced" coating porosity:

| | |
|---|---|
| Water | 25 |
| Sodium Perborate | 1.0 |
| Boric Acid | 1.0 |
| Sodium silicate solution | 56 |
| (40% solids, SiO2/Na2O = 2.5) | |
| Pigments | 5 |
| Kaolin clay | 25 |

Essentially, the same $2^{nd}$ coat formulation, but devoid of sodium perborate and boric acid, was used to prepare A-901 of "standard" coating porosity.

To determine the effect of both "standard" and "porosity enhanced" plant-made A-901 on actual algae growth rates, the following procedure was used:
1. The A-901 granules under test were weatherometer-conditioned as described in the previous example.
2. The conditioned A-901 granules were blended with standard accent-tone granules at both 10% and 15% blend rates.

3. The blended granules were placed in nutrient solutions and inoculated for liquid culture study, also as described in the previous example. The inoculant used was the stock developed from a Tampa roof sample containing a mixture of unicellular Gloeocapsa and filamentous Phormidium Cyanobacteria.
4. After 3 weeks, quantitative spectrophotometric chlorophyll measurements were made to ascertain algae growth rates, which are summarized below:

| Product Blend Rate | Outer Coating Porosity | Chlorophyll Microgram/ml |
| --- | --- | --- |
| Plant-made A-901 @ 10% | Standard | 3.09 |
| Plant-made A-901 @ 10% | Enhanced | 2.31 |
| Plant-made A-901 @ 15% | Standard | 3.29 |
| Plant-made A-901 @ 15% | Enhanced | 1.29 |

At both blend rates studies, the A-901 with the outer coating of enhanced porosity maintained a significantly lower chlorophyll content, which translates to less algae per unit time (growth rate) as a result of increased copper release.

Various modifications of the present invention will become apparent to those skilled in the art without departing from the spirit and scope of the invention as defined in the appended claims.

What is claimed is:

1. Algae-retardant roofing granules having an enhanced ability, over an extended period of time, to release algicidal metallic or bimetallic ions to inhibit the growth of algae and fungi upon atmospheric exposure of roofing surfaces coated with said granules comprising:
    a) a base material of crushed mineral or synthetic aggregates in the form of granules coated with a first or inner layer and a second or outer layer;
    b) said first or inner layer comprising a semi-ceramic composition consisting of a fired silicate-clay matrix containing: of from about 80 pounds to about 180 pounds of cuprous oxide per ton of said base material; or from about 5 pounds to about 40 pounds zinc sulfide admixed with of from about 80 pounds to about 180 pounds of cuprous oxide per ton of said base material; and
    c) said second or outer layer comprising a semi-ceramic composition comprising a fired silicate-clay matrix containing: of from about 0.25 to about 2.5 pounds of an internal gas forming compound per ton of said base materials selected from the group consisting of hydrogen peroxide, alkali metal perborates, alkali metal persulfates, alkali metal borohydrides, and alkali metal azides, wherein said internal gas forming compounds form microvoids in said second or outer layer thereby rendering the second or outer layer porous to allow passage of algicidal copper or zinc ions from said first or inner layer therethrough; and of from about 1 to about 20 pounds of a pigment per ton of said base material.

2. The algae-retardant roofing granules of claim 1 wherein said microvoids in said second or outer layer have an average thickness of from about 0.05 micron to about 0.5 micron.

3. The algae-retardant roofing granules of claim 1 wherein said first or inner layer contains of from about 100 to about 150 pounds of cuprous oxide per ton of base material, and from about 12 to about 25 pounds of zinc sulfide per ton of base material.

4. The algae-retardant roofing granules of claim 1 wherein said pigment is selected from the group consisting of carbon back, titanium dioxide, chromium oxide, yellow iron oxide, ultramarine blue, red iron oxide, black iron oxide, chrome titanate, and metal ferrites.

5. The algae-retardant roofing granules of claim 1 wherein said second or outer layer contains sodium perborate tetrahydrate in mixture with boric acid, or a mixture of hydrogen peroxide and borax.

6. The algae-retardant roofing granules of claim 1 wherein said second or outer layer contains sodium azide or sodium borohydride.

7. The algae-retardant roofing granules of claim 1 wherein said second or outer layer optionally further comprises: from about 80 pounds up to as high as 180 pounds of cuprous oxide per ton of said base material; or of from about 5 pounds to about 40 pounds of zinc sulfide admixed with of from about 80 pounds to about 180 pounds of cuprous oxide per ton of said base material.

8. A method of preparing algae-retardant roofing granules having an enhanced ability, over an extended period of time, to release algicidal metallic or bimetallic ions to inhibit the growth of algae or fungi upon atmospheric exposure of roofing surfaces coated with said granules comprising the steps of:
    a) crushing and sizing a base mineral aggregate to form granules therefrom;
    b) preheating the granules to about 210° F.–230° F.;
    c) coating the preheated granules with a first coat of semi-ceramic composition of an aqueous slurry comprising:
        about 75 pounds of 38% w/w solids sodium silicate solution per ton of said base mineral aggregate,
        about 35 pounds Kaolin clay per ton of said base mineral aggregate,
        about 80–150 pounds cuprous oxide per ton of said base mineral aggregate,
        about 0–25 pounds zinc sulfide per ton of said base mineral aggregate; and
        about 0–10 pounds of pigments per ton of said base mineral aggregate;
    d) pre-drying the first coated granules to a moisture content of about 0.2% to 0.5% w/w;
    e) kiln-firing the pre-dried granules at a temperature of from about 740° F. to about 760° F. to form an insolubilized silicate-clay mixture coating in which the cuprous oxide, zinc sulfide and pigments are uniformly distributed;
    f) cooling the kiln-fired, first coated granules to a temperature of from about 210° F. to 230° F. in preparation for application for a second or outer coating;
    g) coating the cooled granules with a second coat of a semi-ceramic composition of an aqueous slurry comprising:
        about 40 pounds sodium silicate per ton of said base mineral aggregate,
        about 25 pounds of Kaolin clay per ton of said base mineral aggregate,
        about 0.5–1.5 pounds of an internal gas forming compound selected from the group consisting of hydrogen peroxide, alkali metal perborates, alkali metal persulfates, alkali metal borohydrides, and alkali metal azides per ton of said base mineral aggregates, said internal gas forming compounds forming microvoids thereby rendering the coating porous to allow passage of algicidal copper or zinc ions from said inner coat therethrough, about 0.5–1.5 pounds of a solubilizer/stabilizer per ton of said base mineral aggregate, and about 0–15 pounds of a pigment per ton of said base mineral aggregate;

h) pre-drying the second coated granules to a moisture content of about 0.2 to 0.5% w/w;

i) kiln-firing the granules at a temperature of from about 890° F. to about 910° F. to form an insolubilized silicate-clay matrix;

j) reducing the temperature of the granules to about 200° to 220° F.; and k) treating the granules with a mixture of processed oil and an organosilicone compound to impart dust control and adhesion to a substrate.

9. A method of protecting asphalt-coated roof shingles against algae and fungi comprising the steps of:

a) providing asphalt coated roof shingles;

b) providing a base mineral aggregate and forming granules therefrom;

c) coating said granules with a first layer of a semi-ceramic composition consisting of a fired silicate-clay matrix containing: of from about 80-pounds to about 180 pounds of cuprous oxide per ton of said base mineral aggregate; or from about 5 pounds to about 40 pounds of zinc sulfide admixed with of from about 80 pounds to about 180 pounds of cuprous oxide per ton of said base mineral aggregate;

d) coating said first layer coated granules with a second layer of a semi-ceramic composition consisting of a fired silicate-clay matrix containing:

of from about 0.5 to about 1.5 pounds of an internal gas-forming compound per ton of said base minerals aggregate selected from the group consisting of hydrogen peroxide, alkali metal perborates, alkali metal persulfates, alkali metal borohydrides, and alkali metal azides wherein said internal gas-forming compounds form microvoids in said second or outer layer thereby rendering the second or outer layer porous to allow passage of algicidal copper or zinc ions from said first layer therethrough, about 56 pounds of 40% w/w solids sodium silicate solution per ton of said base mineral aggregate, about 25 pounds of Kaolin clay per ton of said base mineral aggregate, about 0.5–1.5 pounds of a solubilizer/stabilizer per ton of said base mineral aggregate, and about 0–15 pounds of a pigment per ton of said base mineral aggregate;

e) treating said first and second layer coated granules with a mixture of process oil and an organosilicone compound to impart dust control and adhesive properties thereto to obtain treated granules ready for coating said asphalt coated roof shingles; and f) applying said treated granules to said roofing shingles to obtain algae and fungi-resistant roof shingles.

* * * * *